United States Patent [19]  
Clark

[11] 4,113,972  
[45] Sep. 12, 1978

[54] ESTERS OF DERIVATIVES OF 1,1-DIPHENYL-3-AMINO-PROPAN-2-OL

[75] Inventor: Judith Ann Clark, Barrington, England

[73] Assignee: Beecham Group Limited, England

[21] Appl. No.: 698,091

[22] Filed: Jun. 21, 1976

Related U.S. Application Data

[62] Division of Ser. No. 443,021, Feb. 15, 1974, Pat. No. 4,028,415.

[30] Foreign Application Priority Data

Feb. 24, 1973 [GB] United Kingdom ............... 9183/73  
Oct. 13, 1973 [GB] United Kingdom ............. 47928/73

[51] Int. Cl.$^2$ .................. C07C 93/00; C07C 93/26

[52] U.S. Cl. .................. 560/250; 560/173; 560/251; 260/243.3; 560/252; 260/293.73; 260/293.79; 260/293.81; 260/293.83; 260/293.84; 260/326.49; 260/326.5 L; 260/326.5 R; 260/326.5 S; 424/248.56; 424/250; 424/267; 424/274; 424/311; 424/325; 424/248.52; 424/248.53; 424/248.55; 544/158; 544/170; 544/171; 544/172; 544/173; 544/174; 544/372; 544/360; 544/396; 560/36; 560/105; 560/107; 560/140

[58] Field of Search ............... 260/490, 477; 560/105, 560/107, 250

[56] References Cited

U.S. PATENT DOCUMENTS 3,395,146   7/1968   Satzinger ..................... 260/490

OTHER PUBLICATIONS

Greenhill, J. Chem. Soc. (London), Sect. C, (1970), pp. 1298–1301.

*Primary Examiner*—Vivian Garner  
*Attorney, Agent, or Firm*—Jacobs & Jacobs

[57] ABSTRACT

1,1-Diphenyl-2-hydroxy-3-aminopropane derivatives are useful for their psychotropic activity and, in particular are useful as antidepressants.

15 Claims, No Drawings

ESTERS OF DERIVATIVES OF 1,1-DIPHENYL-3-AMINO-PROPAN-2-OL

CROSS-REFERENCE

This is a division of Ser. No. 443,021 filed Feb. 15, 1974, now U.S. Pat. No. 4,028,415.

The present invention relates to derivatives of 1,1-diphenyl-2-hydroxy-3-aminopropane which possess useful psychotropic activity and which in particular, have mood modifying activity such as mood elevating activity.

Compounds of the formula (I):

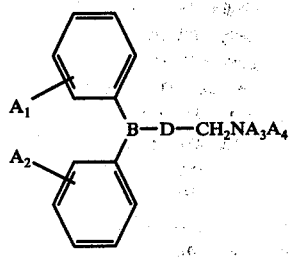

wherein $A_1$ and $A_2$ are halogen or hydrogen atoms or lower alkyl or alkoxy groups; $A_3$ and $A_4$ are hydrogen atoms or methyl groups or together with the nitrogen atom to which they are attached form a 5- or 6-membered rings; and B - D is a $-CH_2.CH_2-$ or $-C:CH-$ group; were shown by Jones et al [J. Med. Chem., 14, 161 (1971)] to possess psychotropic activity. In that same paper, it was suggested that compounds of the formula (II):

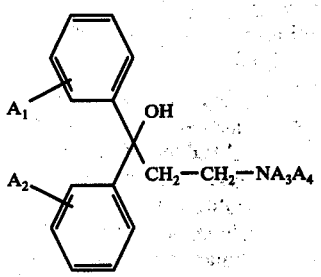

could be used as intermediates in the synthesis of compounds of the formula (I) but it was not suggested that the compounds of formula (II) might have psychotropic activity. This may well have been because such compounds were structurally further removed from the amitriptyline type structure that the compounds of formula (I) were alleged to possess.

However, U.K. Pat. No. 1,025,051 and its Patent of Addition No. 1,039,454 disclose that certain of the compounds of the formula (I) and related butylamines have anticonvulsant, antidepressant and diuretic activity. One particularly active compound prepared in the Patent Addition was 1:1-diphenyl-3-dimethylaminopropan-1-ol and its activity was further demonstrated by Barron et al [J. Pharm. Pharmacol., 17, 509 (1965)]. The authors confirmed that the compound had considerable effects on the central nervous system but their results show that the compound also suffered from side effects such as anorexia, diuresis, ataxia and drowsiness. These effects were so high that the investigation of the compound was discontinued.

U.K. Pat. No. 624,118 suggested that certain of the compounds of formula (II) might possess bronchodilating properties. Such a suggestion was not unreasonable as benzylic alcohols frequently have pharmacological activity and especially bronchodilatory activity. However, compounds of formula (II) have not found use as bronchodilators.

It was suggested by Lutz et al [J. Org. Chem., 12, 767 (1949)] that compounds of formula (II) might have antimalarial activity but no activity of clinical significance has been reported.

Greenhill [J. Chem. Soc. (C), 1298 (1970)] disclosed a series of compounds which contain an alkanolic hydroxyl group in addition to or in place of the benzylic hydroxyl group. The author had hoped that such compounds might possess pharmacologically useful activity because they had some relationship to the benzylic alcohol Benzhexol which was said to possess anti-Parkinson activity. However, the author was forced to report that although the compounds had been pharmacologically tested, "no marked activity had been discovered".

As may be seen in the foregoing section certain diphenylpropylamine derivatives have previously been examined in a search for therapeutic agents but to date none have found a place in medicine. It is thus surprising that one group of such compounds has now been found to possess useful mood modifying activity. It has further been found that this group of compounds is able to produce a mood elevating effect while being free or substantially free of peripheral anti-cholinergic activity. The useful compounds may be administered in the form of an orally or parenterally administrable pharmaceutical composition.

One of the objects of this invention is to provide pharmaceutical compositions which on administration to mammals are capable of producing a psychotropic effect and in particular, produce a mood elevating effect without causing substantial side effects such as those associated with anti-cholinergic agents.

Accordingly, the present invention provides a pharmaceutical composition which comprises a pharmaceutically acceptable carrier in association with a compound of the formula (III):

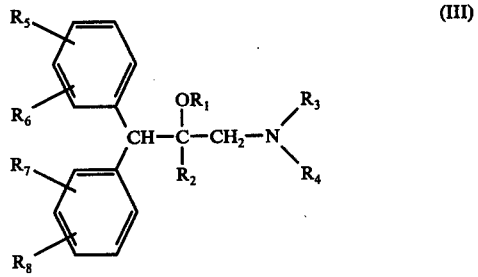

wherein $R_1$ is a hydrogen atom or a group $R_9$ or $CO.R_9$ wherein $R_9$ is a $C_{1-6}$ alkyl phenyl or benzyl group or such a group $\omega$-substituted by a group $NR_{10}R_{11}$ where $R_{10}$ is a hydrogen atom or a methyl, ethyl or benzyl group and $R_{11}$ is a hydrogen atom or a methyl or ethyl group or is attached to $R_{10}$ so that $NR_{10}R_{11}$ is a pyrrolidyl, piperidyl, morpholino or hexamethylenimino group; $R_2$ is a hydrogen atom or a methyl or ethyl group; $R_3$ is a hydrogen atom or a methyl ethyl propyl or benzyl group; $R_4$ is a hydrogen atom or a methyl or ethyl group or is attached to $R_3$ so that $NR_3R_4$ is a pyrrolidyl, piperidyl, morpholino, N-methylpiperazino or hexamethylenimino group $R_5$ is a hydrogen, fluorine, chlorine or bromine atom or a methyl, ethyl, propyl, butyl, benzyl, trifluoromethyl, hydroxy, methoxy, ethoxy, propoxy, benzyloxy, acetoxy, propionoxy, amino, methylamino, ethylamino, dimethylamino, diethylamino, carboxyl, methoxycarbonyl, ethoxycarbonyl, propoxycarbonyl, nitro or methylthiol group $R_6$, $R_7$ and $R_8$ which may be the same or different are each a hydrogen, fluorine, chlorine or bromine atom or a methyl, ethyl, methoxy, ethoxy, acetoxy, hydroxy or trifluoromethyl group; or a salt or solvate thereof.

Acid salts of compounds of formula (III) include those of pharmaceutically acceptable organic or inorganic acids such as sulphuric, hydrochloric, hydrobromic, phosphoric, acetic, propionic citric, malonic, malic, lactic, methanesulphonic toluenesulphonic, tartaric or any similar acid.

Solvates if formed, are normally and preferably hydrates.

Most suitably $R_1$ is a hydrogen atom or a group $CO.R_9$ where the most suitable groups $R_9$ are the methyl, ethyl, $CH_2CH_2NR_{10}R_{11}$ or $CH_2CH_2CH_2NR_{10}R_{11}$ groups where $R_{10}$ is a hydrogen atom or a methyl or ethyl group and $R_{11}$ is a methyl or ethyl group or $NR_{10}R_{11}$ is a piperidyl group.

Preferably $R_1$ is a hydrogen atom.

Most suitably $R_2$ is a hydrogen atom or methyl group.

Preferably $R_2$ is a hydrogen atom.

Most suitably $R_3$ is a hydrogen atom or a methyl or benzyl group; $R_4$ is a hydrogen atom or a methyl or ethyl group.

Preferably $R_3$ is a hydrogen atom or a methyl group.

Preferably $R_4$ is a methyl group.

Most suitably $R_5$ is a hydrogen, fluorine, chlorine or bromine atom or a methyl, ethyl, trifluoromethyl, methoxy, ethoxy, acetoxy, nitro, amino, methylamino or dimethylamino group.

Most suitably $R_6$, $R_7$ and $R_8$ are selected from hydrogen, fluorine, chlorine or bromine atoms or methyl, methoxyl or trifluoromethyl groups.

Certain preferred compositions of this invention contain a compound of the formula (IV):

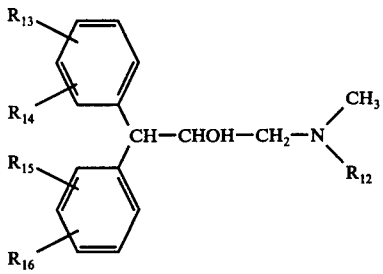

wherein $R_{12}$ is a hydrogen atom or a methyl group and $R_{13}$ $R_{14}$ $R_{15}$ and $R_{16}$ which may be the same or different are each a hydrogen, fluorine, chlorine or bromine atom or a methyl trifluoromethyl or methoxyl group or a salt thereof or O-acetyl derivative thereof.

Most suitably $R_{13}$ is a hydrogen, fluorine, chlorine or bromine atom or a methyl or trifluoromethyl group.

Most suitably $R_{14}$ is a hydrogen, chlorine or bromine atom.

Preferably $R_{14}$ is a hydrogen atom.

Most suitably $R_{15}$ is a hydrogen, fluorine, chlorine or bromine atom or a trifluoromethyl group.

Preferably $R_{15}$ is a hydrogen, fluorine or chlorine atom and most preferably, a hydrogen atom.

Most suitably $R_{16}$ is a hydrogen atom.

Compounds of formula (IV) of particularly useful activity are included among those compounds wherein $R_{14}$, $R_{15}$ and $R_{16}$ are each hydrogen atoms and $R_{13}$ is a hydrogen, fluorine, bromine or chlorine atom or a trifluoromethyl group.

Preferred compounds for inclusion within the compositions of this invention include those of formula (IV) wherein $R_{14}$, $R_{15}$ and $R_{16}$ are each hydrogen atoms and $R_{13}$ is a hydrogen, 4-fluorine, 3- or 4-chlorine, 3-bromine atom or a 3-trifluoromethyl group.

The compounds of formula (III) have a center of assymetry at the 2-carbon atom and those compounds in which the two phenyl rings are differently substituted have a further centre of assymetry at the 1-carbon atom. A pure optical isomer may be used in the compositions of this invention if desired or else mixtures of isomers may be use. Fully racemic mixtures have the advantage of ease of preparation but individual isomers or pairs of enantiomers can have certain differences in activity and rate of onset of action that makes their use in the compositions of the invention beneficial.

The compounds of formula (III) may advantageously be included in the solid composition of the invention in the form of a crystalline acid addition salt.

The compositions of the invention are specially useful in treating adverse mental states such as, for example, depressive conditions. For such treatment, the compounds are generally administered orally although parenteral methods of administration may also be used.

Typical oral formulations will include tablets, pills, capsules, sachets, granules, powders, chewing gum, suspensions, emulsions and solutions; particularly preferred oral formulations are tablets and capsules. Where appropriate, the formulations may include conventional diluents, binding agents, dispersing agents, surface-active agents, lubricating agents, coating materials, flavouring agents, coloring agents, solvents, thickening agents, suspending agents, sweeteners or any other pharmaceutically acceptable additives, for example, gelatin, lactose, starch, talc, magnesium stearate, hydrogenated oils, polyglycols and syrups. Where the formulations are tablets or capsules and the like, they will represent pre-measured unit doses, but in the case of granules, powders, suspensions and the like, the formulations may be presented as pre-measured unit doses or in multi-dose containers from which the appropriate unit dose may be withdrawn.

Injectable compositions may be as aqueous or non-aqueous solutions, suspensions or emulsions in a pharmaceutically acceptable liquid (e.g. sterile pyrogen-free water or parenterally acceptable oils) or mixtures of liquids which may contain bacteriostatic agents, antioxidants or other preservatives, buffers, (preferably in the physiological pH range of 6.5 - 7.0), solutes to render the solution isotonic with the blood, thickening agents, suspending agents or other pharmaceutically acceptable additives. Such forms will be presented in unit dose forms such as ampoules or disposable injection devices or in multi-dose forms such as a bottle from which the appropriate dose may be withdrawn, or as a solid form or concentrate which can be used to quickly prepare an injectable formulation.

Suppositories containing the compound will also contain suitable carriers (e.g. cocoa-butter or polyglycols).

In general, the compositions of the invention will usually have associated with them, directions for use as antidepressive medications.

Preferred dosage forms of the composition will be conventional tablets or capsules containing a premeasured dose for oral administration. Such dosage forms will normally contain between 1 and 100 mgs of compound of formula (III) and generally between 2.5 and 75 mgs. preferably from about 5 to about 50 mgs. Such dosage forms will normally be taken from 1 to 6 times daily. The maximum daily dose for a 70 kg adult will not normally exceed 360 mgs. and will not usually exceed 250 mgs. A daily dose of not more than 150 mgs. is generally preferred. Normally, the daily dose for a 70 kg adult will be at least 25 mgs., usually at least 5 mgs.

The compositions of the invention may be prepared by conventional methods of mixing, blending, tabletting and the like.

Compounds of formula (III) are novel except those wherein $R_2$, $R_5$, $R_6$, $R_7$ and $R_8$ are all hydrogen atoms and either (a) $R_1$ is a hydrogen atom and $NR_3R_4$ is a dimethylamino, diethylamino or morpholino group or (b) $R_1$ is an acetyl group and $NR_3R_4$ is a dimethylamino group. Such novel compounds and their salts form a part of this invention.

The most suitable and preferred values for $R_1 - R_8$ of these new compounds are the same as those stated as suitable and preferable in association with the compounds of formula (III).

A preferred group of novel compounds of the invention are those of formula (IV) as previously defined except that $R_{12}$ is not methyl when $R_{13}$, $R_{14}$, $R_{15}$ and $R_{16}$ are all hydrogen.

The most suitable and preferred values in the compounds for $R_{13}$, $R_{14}$, $R_{15}$ and $R_{16}$ of these novel compounds are as previously defined.

As previously stated, compounds of formula (III) can exist as pure optical isomers or mixtures of isomers. When a compound of formula (III) exists as an optical isomer, substantially free of alternative optical isomers, it is novel and forms part of this invention. Further, if the compounds of formula (III) are capable of existing as a mixture of four optical isomers, this invention includes each optical isomer in substantially pure form or mixtures of two or three such isomers.

The present invention includes as one of its aspects, a process for the preparation of compounds of formula (III) as hereinbefore defined except that when $R_2$, $R_5$, $R_6$, $R_7$ and $R_8$ are all hydrogen and either (a) $R_1$ is a hydrogen atom and $NR_3R_4$ is a dimethylamino, diethylamino or morpholino group, or (b) $R_1$ is an acetyl group and $NR_3R_4$ is a dimethylamino group; which process comprises the condensation of an amine of the formula $HNR_3R_4$ with a compound of the formula (V):

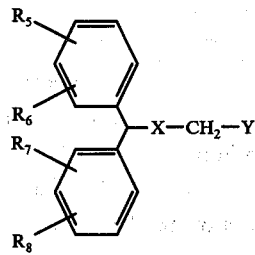

(V)

or a salt thereof wherein $R_5$, $R_6$, $R_7$ and $R_8$ are as defined in relation to formula (III), Y is a group displaceable by a neucleophile and X is a group $CR_2OR_1$ or a suitable precursor thereof; and thereafter if desired, converting any of the groups $R_1$, $R_2$, $R_3$, $R_4$, $R_5$, $R_6$, $R_7$, and $R_8$ to alternative groups $R_1$, $R_2$, $R_3$, $R_4$, $R_5$, $R_6$, $R_7$ and $R_8$ by known methods and if X is a precursor of $CR_2OR_1$, converting X to $CR_2OR_1$ by known methods.

Suitable groups Y include chlorine, bromine or iodine atoms, pseudohalides such as azide activated oxygen atoms such as one present in an epoxide or present in reactive esters such as methylsulphonyl or toluene sulphonyl esters or reactive derivatives formed from a hydroxyl group and a dehydrating agent such as a carbodiimide or imidazolediimide or the like, or any other such known good leaving groups.

If Y is a particularly good leaving group such as an iodine atom or that produced by the reaction of a compound wherein Y is hydroxyl with a carbodiimide, it is preferable that X is not a $CR_2OH$ group in order that self-condensation is minimized.

Suitable groups X which are precursors of the groups $CR_2OR_1$ include the carbonyl group and groups $CR_2OR^1$ and $CR_2OCOR^1$ where $R^1$ is an inert optionally substituted hydrocarbon group such that the intermediate is hydrolysable or reduceable to the alcohol. When X is a carbonyl group, reduction to the alcohol may take place under conventional conditions.

If desired, the group Y may be linked to the group X so that $XCH_2Y$ is a

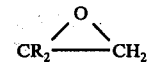

group.

Suitable transformations of groups $R_5$, $R_6$, $R_7$ and $R_8$ include reduction and alkylative reduction of nitro groups to amino or alkylamino groups; saponification of esters, hydrogenolysis of benzyl ethers and the like.

The group $OR_1$ may be converted from a hydroxyl group to an ether or acyloxy group by conventional methods and the group $OR_1$ may be converted from an ether or acyloxy group to hydroxyl group by conventional methods of hydrolysis or hydrogenolysis or the like.

If desired the groups $R_3$ and $R_4$ may be modified in conventional manner, for example, a primary amino group $NH_2$ or a secondary amino group, for example, $NHR_3$, may be alkylated or acylated in conventional manner or a compound in which one or two of $R_3$ and $R_4$ are already acyl groups may be converted to the amine by conventional methods.

Compounds which may be produced by such processes include:
3-N-Benzyl-N-methylamino-1,1-diphenyl-propan-2-ol
3-Methylamino-1,1-diphenyl-propan-2-ol
3-N-Benzyl-N-methylamino-1-p-fluorophenyl-1-phenylpropan-2-ol
3-Methylamino-1-p-fluorophenyl-1-phenyl-propan-2-ol
3-Di-ethylamino-1-p-fluorophenyl-1-phenyl-propan-2-ol
3-(N-Benzyl-N-methylamino)-2-methyl-1,1-diphenyl-propan-2-ol
3-Methylamino-2-methyl-1,1-diphenyl-propan-2-ol
3-Dimethylamino-1,1-di-p-fluorophenyl-propan-2-ol
3-Dimethylamino-1-phenyl-1-o-tolyl-propan-2-ol
3-Dimethylamino-1-p-chlorophenyl-1-phenyl-propan-2-ol 3-Dimethylamino-1-m-chlorophenyl-1-phenyl-propan-2-ol
3-Dimethylamino-1-phenyl-1-p-tolyl-propan-2-ol
3-(N-Benzyl-N-methylamino)-1-phenyl-1-p-tolyl-propan-2-ol
3-Methylamino-1-phenyl-1-p-tolyl-propan-ol
3-Dimethylamino-1-phenyl-1-m-trifluoromethyl-phenylpropan-2-ol
3-Dimethylamino-1-p-methoxyphenyl-1-phenyl-propan-2-ol
3-Dimethylamino-1-o-chlorophenyl-1-phenyl-propan-2-ol
3-Dimethylamino-1-m-bromophenyl-1-phenyl-propan-2ol
3-Dimethylamino-1-(3,4-dichlorophenyl)-1-phenyl-propan-2-ol
3-N-methyl-N-ethylamino-1,1-diphenyl-propan-2-ol
3-N-piperidino-1,1-diphenyl-propan-2-ol
2-Benzoyloxy-3-dimethylamino-1,1-diphenyl-propane
3-Benzylamino-1,1-diphenyl-propan-2-ol
4-Dimethylaminobutyrate of 3-dimethylamino-1,1-diphenyl-propan-2-ol
3-Dimethylamino-1,1-diphenyl-propan-2-ol
3-Dimethylamino-1-(3,5-dichlorophenyl)-1-phenyl-propan-2-ol
3-Dimethylamino-1-m-nitrophenyl-1-phenyl-propan-2-ol
3-Dimethylamino-1-p-bromophenyl-1-phenyl-propan-2-ol
3-Dimethylamino-1-p-trifluoromethyl-1-phenyl-propan-2-ol
3-Dimethylamino-1,1-diphenylpropan-2-ol 2-β-dimethylaminopropionate A particularly suitable method of preparation of compounds of formula (IV) as previously defined comprises the reaction of a compound of the formula (VI):

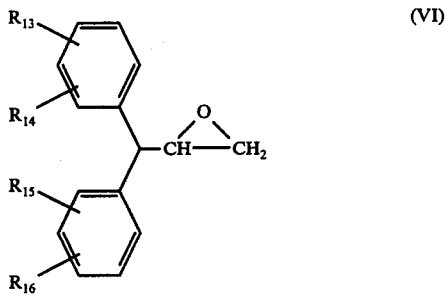
(VI)

With methylamine or dimethylamine or reacting with benzylmethylamine and thereafter removing the benzyl group by hydrogenation.

Reactions strictly analogous to this are suitable for the preparation of other compounds of formula (III) wherein $CR_2OR_1$ is a CHOH group.

Such a reaction is normally carried out in an organic solvent such as a lower alkanol, for example, ethanol.

The reaction may be carried out at any non-extreme low, ambient or elevated temperature. But a temperature of $-10°$ C to $110°$ C is generally preferred, for example, 5° C to 60° C, for example, at room temperature (12° – 18° C).

The epoxide of formula (VI) may be prepared by the reaction of an aldehyde of the formula (VII):

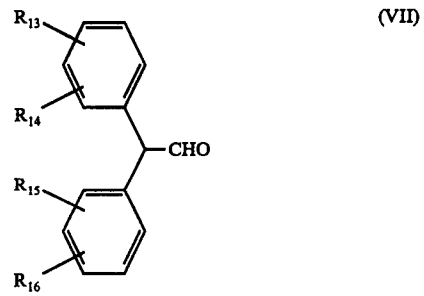
(VII)

wherein $R_5$, $R_6$, $R_7$ and $R_8$ are as defined in relation to formula (IV) with $O = S(CH_3)_2 = CH_2$ or $(CH_3)_2S = CH_2$.

This reaction may take place under the conditions outlined in Fieser & Fieser, "Reagents for Organic Synthesis", published by Wiley, 1967, at pages 314 to 318.

The compounds (VII) may be prepared by the method of Wittig. et al, Chem. Ber., 94, 1373 (1961) or Mislow et al, J. Amer Chem Soc , 74, 1060 (1952).

A process for the preparation of the aldehydes of formula (VII) comprises the contacting of an epoxide of the formula (VIII):

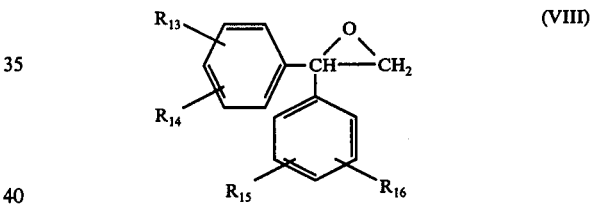
(VIII)

wherein $R_{13}$, $R_{14}$, $R_{15}$ and $R_{16}$ are as defined in relation to formula (VII) with boron trifluoride etherate or equivalent Lewis acid.

Such a reaction will take place in an inert solvent system, for example, benzene. Although any non-extreme temperature may be used, it is generally preferred to use an ambient temperature as the reaction goes to completion in a few minutes under these convenient conditions.

Only a catalytic quantity of the Lewis acid need be used.

The epoxides of formula (VIII) may be prepared from the corresponding benzophenone by reaction with $O = S(CH_3)_2 = CH_2$ or $(CH_3)_2S = CH_2$ under conventional reaction conditions.

The useful intermediates (VII) and (VIII) when novel, also from part of this invention.

A further particularly suitable method of preparing compounds of formula (IV) comprises the reduction of a compound of the formula (IX):

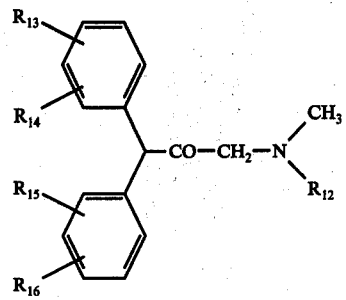

(IX)

wherein $R_{12}$, $R_{13}$, $R_{14}$, $R_{15}$, and $R_{16}$ are as defined in relation to formula (IV) except that $R_{13}$, $R_{14}$, $R_{15}$ and $R_{16}$ are not all hydrogen when $R_{12}$ is a methyl group.

Reactions strictly analogous to this are suitable for the preparation of other compounds of formula (III) where $CR_2OR_1$ is a CHOH group.

Such a reaction may be effected by conventional means, for example, by the use of hydrogen and a transition metal catalyst or by the action of a complex hydride such as sodium borohydride or the like. The reactions are normally carried out in an organic solvent such as an alkanol for example, methanol or ethanol. Such reactions are normally carried out at any non-extreme low ambient or elevated temperature. But a temperature of $-10°$ C to $110°$ C is generally preferred, for example, $5°$ C to $60°$ C, for example at room temperature ($12°-18°$ C).

The amine (IX) may be prepared by the reaction of dimethylamine or benzylmethylamine with a compound of the formula (X):

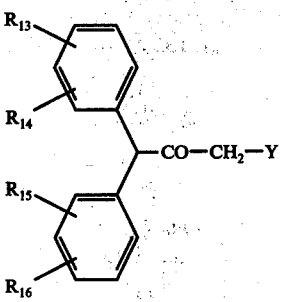

(X)

where Y is as previously defined in relation to formula (V) and $R_{13}$, $R_{14}$, $R_{15}$ and $R_{16}$ are as defined in relation to formula (IX) and when benzylmethylamine is used, cleaving the benzyl group by hydrogenation.

Such a reaction is normally carried out in an organic solvent at a non-extreme temperature.

The compounds of formula (X) wherein Y is a halogen atom may be prepared from the corresponding methyl ketone by the method of Stevens et al [J. Org Chem., 19, 538 (1954)] or analogous methods. Other compounds of formula (X) may be prepared from the bromo- or chloroketone in conventional manner.

The novel intermediates (IX) also form an aspect of this invention.

Compounds of formula (IV) may also be prepared by reductive alkylation of a corresponding N-desmethyl compound for example, by reducing a mixture of formaldehyde and an amine of formula (IV) wherein $R_{12}$ is hydrogen or the corresponding primary amine.

Compounds of formula (IV) wherein $R_{12}$ is a hydrogen atom may also be prepared by the catalytic hydrogenation of the corresponding benzylamine.

Compounds of the formula (II) in which X is a $CHOCOR_9$ group may be prepared by reaction of a compound of the formula (II) in which X is CHOH and Y is a displaceable group with a reactive acylating derivative of an acid of the formula $HO.CO.R_9$ or salt thereof the conventional manner followed by reaction with an amine of the formula $HR_3R_4$. Alternatively such compounds may be prepared by the acylation of an acid addition salt of the corresponding compound wherein X is CHOH.

In addition to being useful pharmaceutical agents in their own right, the compounds of formula (III) when prepared as a mixture of optical isomers, also serve as useful intermediates in the preparation of their substantially pure optical isomers or optically active mixture of such isomers.

Compounds of the formula (III) may normally be resolved by conventional techniques used by those skilled in such work. For example, they teach useful methods of resolution.

Compounds of the formula (IV) wherein the two optionally substituted phenyl groups are the same can be resolved into d- and l- forms by the use of an appropriate resolving agent such as an optically active acid. Alternatively compounds of formula (IV) wherein the two optically substituted phenyl groups are different may be separated into erythro and threo forms by for example fractional crystallisation of a salt. Resolution of erythro and threo forms into d- and l- isomers could then be achieved by the use of an appropriate resolving agent.

Particularly suitable resolving acids include (+)-mandelic and (−)-mandelic acid.

EXAMPLE 1

3-(N-Benzyl-N-methylamino)-1,1-diphenyl-propan-2-ol

Benzylmethylamine (97g) was added to a solution of 3-bromo-1,1-diphenylpropan-2-one (3 9g) in ether (80 ml.) and the mixture stirred for 4 hours. Extraction with dilute hydrochloric acid followed by basification and subsequent extraction into ether gave an oil which was chromatographed on silica gel (400g). Elution with progressively graded mixtures of light petroleum and ether gave 3-(N-benzyl-N-methylamino)-1,1-diphenyl-propan-2-one characterised as the hydrochloride (3 8g., 85%), m p 179° − 183° (from ethanol-ether).

Sodium borohydride (1 2g) in water (15 ml.) was added to a solution of 3-N-benzyl-N-methylamino-1,1-diphenyl-propan-2-ol hydrochloride (3 8g) in methanol (80 ml.) and the mixture stirred for 1 hour. Concentrated hydrochloric acid (4 ml.) was then added and the solution evaporated under reduced pressure. The residue was dissolved in water; the aqueous solution ws washed with ether, basified and extracted into ether. 3-(N-Benzyl-N-methylamino)-1,1-diphenyl-propan-2-ol was obtained which was characterised as the hydrochloride (3 1g , 80%), m p 158°−161° (from ethanol-ether).

EXAMPLE 2

3-Methylamino-1,1-diphenyl-propan-2-ol

A solution of 3-N-benzyl-N-methylamino-1,1-diphenylpropan-2-ol hydrochloride (2g.) in ethanol (50 ml.) was hydrogenated at atmospheric pressure and room temperature over 5% palladium on charcoal (200 mg) for 24 hours.

Filtration and evaporation gave 3-methylamino-1,1-diphenyl-propan-2-ol isolated as the hydrochloride (1.1g., 75%) m p 187° – 188° (from ethanol-ether).

EXAMPLE 3

3-(N-Benzyl-N-methylamino)-1-p-fluorophenyl-1-phenyl-propan-2-ol

Bromine (14 85g) in acetic acid (200 ml.) was added dropwise to a solution of 1-p-fluorophenyl-1-phenyl-propan-2-one (20 1g.) in acetic acid (200 ml.) at 60° – 70°. After 30 minutes, the reaction mixture was poured on to ice. Isolation through ether in the usual manner gave crude 3-bromo-1-p-fluorophenyl-1-phenyl-propan-2-one (28g) which was converted by the procedures described in Example 1 to 3-(N-Benzyl,N-methylamino)-1-p-fluorophenyl-1-phenyl-propan-2-ol (38%), m.p. 61° – 62°.

EXAMPLE 4

3-Methylamino-1-p-fluorophenyl-1-phenyl-propan-2-ol

Hydrogenation of 3-(N-benzyl,N-methylamino)-1-p-fluorophenyl-1-phenyl-propan-2-ol by the procedure described in Example 2 gave 3-methylamino-1-p-fluorophenyl-1-phenyl-propan-2-ol isolated as the hydrochloride (70%) as a glass.

EXAMPLE 5

3-Dimethylamino-1-p-fluorophenyl-1-phenyl-propan-2-ol

Dimethylamine in ethanol (30 ml s of 33% solution) was added to a solution of 3-bromo-1-p-fluorophenyl-1-phenyl-propan-2-one (13g) in dry ether. After 45 minutes, the reaction mixture was extracted with dilute hydrochloric acid and ether. Basification of the acid extract and subsequent isolation through ether in the usual manner gave 3-dimethylamino-1-p-fluorophenyl-1-phenyl-propan-2-one isolated as the hydrochloride (5 8g., 53%), m.p. 219° – 220°.

Reduction with sodium borohydride by the procedure described in Example 1 followed by chromatography on alumina using progressively graded mixtures of light petroleum and ether as eluant gave 3-dimethylamino-1-p-fluorophenyl-1-phenyl-propan-2-ol (76%), m.p. 55° – 57°.

EXAMPLE 6

3-(N-Benzyl-N-methylamino)-2-methyl-1,1-diphenyl-propan-2-ol 3-(N-Benzyl-N-methylamino)-1,1-diphenyl-propan-2-one (10g) in dry ether (250 ml.) was added to a solution of methyl magnesium iodide (from 2.4g. magnesium and 14 2g methyl iodide) in dry ether (250 ml.) and the mixture heated at reflux for 2 hours. Saturated ammonium chloride solution was added; isolation through ether in the usual manner gave 3-(N-benzyl,N-methylamino)-2-methyl-1,1-diphenyl-propan-2-ol, purified by chromatography on alumina using progressively graded mixtures of light petroleum and ether as eluant and isolated as the hydrochloride (6 8g , 65%), m.p. 121° – 124° (from ethanol-ether).

EXAMPLE 7

3-(N-methylamino)-2-methyl-1,1-diphenyl-propan-2-ol

Hydrogenation of 3-(N-benzyl,N-methylamino)-2-methyl-1, 1-diphenyl-propan-2-ol by the procedure described in Example 2 gave 3-methylamino-2-methyl-1,1-diphenyl-propan-2-ol isolated as the hydrochloride (79%), m.p. 272°– 273°.

EXAMPLE 8

3-Dimethylamino-1,1-di-4-fluorophenyl-propan-2-ol

Phenyl lithium (20 ml of 1M solution in ether) was added under nitrogen to a stirred suspension of methoxymethyltriphenylphosphonium chloride (6 88g) in dry ether. After 10 minutes, 4,4-difluorobenzophenone (4.56g) in dry ether was added. After a further 2 hours, triphenylphosphine oxide was filtered off and the filtrate evaporated. The residue was chromatographed on alumina to yield 1,1-di-4-fluorophenyl-2-methyoxyethylene (3g, 59%) which was dissolved in a solution of 10% sulphuric acid in acetic acid (50ml) and allowed to stand for 30 minutes. Isolation through ether in the usual manner yielded 1,1-di-4-fluorophenylacetaldehyde which was purified by chromatography on silica gel (2,2g., 78%).

1,1 Di-4-fluorophenylacetaldehyde (2.2g.) in dimethyl sulphoxide (10 ml) was added under nitrogen to a solution of dimethylsulphoxonium methylide (prepared from 2.5g. trimethylsulphoxonium iodide and 450 mg of 60% sodium hydride in 20 ml of dimethylsulphoxide) and the mixture heated at 50° for one hour. Isolation through ether yielded crude epoxide which was dissolved in a solution of dimethylamine in ethanol (10 mls. of 33% solution) and allowed to stand for 24 hours. Evaporation of solvent and extraction of the residue with dilute acid allowed the isolation of 3-dimethylamino-1,1-di-(4-fluorophenyl)-propan-2-ol (1 4g. 55%), m.p. 56° – 58° purified by chromatography on alumina.

EXAMPLE 9

3-Dimethylamino-1-phenyl-1-o-tolyl-propan-2-ol

1-Phenyl-1-o-tolyl-acetaldehyde was reacted with dimethylsulphoxonium methylide and the crude epoxide obtained reacted with dimethylamine by the procedures described in Example 5. 3-Dimethylamino-1-phenyl-1 -o-tolyl-propan-2-ol was isolated as the hydrochloride, m.p. 218° – 219° (58%).

EXAMPLE 10

3-Dimethylamino-1-p-chlorphenyl-1-phenyl-propan-2-ol p Chlorobenzophenone (8 65g) in dimethylsulphoxide (15ml) was added under nitrogen to a solution of dimethylsulphoxanium methylide (from 10 55g of trimethylsulphoxonium iodide and 1 15g of sodium hydride) and the mixture heated at 50° for 2 hours. Isolation through ether yielded crude 1,2-epoxy-1-p-chlorophenyl-1-phenylethane (9 0g).

Borontrifluoride etherate (5 drops) was added to a solution of the crude epoxide (9 0g) in dry benzene (250 ml). After 5 minutes water was added and the benzene layer washed with water until no longer acidic. Evaporation of solvent gave an oil which was chromatographed on silica gel; elution with progressively graded mixtures of light petroleum and ether yielded p- chlorophenyl-phenylacetaldehyde (5 68g 62%9 as an oil.

p-Chlorophenyl-phenylacetaldehyde (5 68g) was reacted with dimethylsulphoxonium methylide and the crude epoxide obtained further reacted with dimethylamine in ethanol by the procedures described in Example 8 to give 3-dimethylamino- 1-p-chlorphenyl-1-phenyl-propan-2-ol (2.6g., 37% from aldehyde) as an oil.

EXAMPLE 11

3-Dimethylamino-1-m-chlorophenyl-1-phenyl-propan-2-ol

An identical sequence of reactions to those described in Example 10 was used to convert m-chlorobenzophenone to 3-dimethylamino-1-m-chlorophenyl-1-phenyl-propan-22-ol isolated as the hydrochloride (24%), m.p. 118° – 123° (from ethanol-ether). No intermedites were purified.

EXAMPLE 12

3-Dimethylamino-1-phenyl-1-p-tolyl-propan-2-ol

Following the procedures described in Examples 3 and 5, 1-phenyl 1-p-tolyl-propan-2-one as converted to 3-dimethylamino-1-phenyl-1-p-tolyl-propan-2-ol (30%), m.p. 55° – 58°.

EXAMPLE 13

3-(N-Benzyl N-methylamino)-1-phenyl-1-p-tolyl-propan-2-ol

Following the procedures described in Examples 3 and 1, -phenyl,1-p-tolyl-propan-2-one was converted to 3-(N-benzyl-N-methylamino)-1-phenyl-1-p-tolyl-propan-2-ol (25%) obtained as an oil.

EXAMPLE 14

3-N-methylamino-1-phenyl-1-p-tolyl-propan-2-ol

Hydrogenation of 3-(N-Benzyl-N-methylamino)-1-phenyl-1-p-tolyl-propan-2-ol by the procedures described in Example 4 gave 3-N-methyamino-1-phenyl-1-p-tolyl-propan-2-ol isolated as the hydrochoride. Recrystallisation from ethanol-ether gave two crops m.p. 186°– 188° (35%) and m.p. 150°– 152° (36%).

EXAMPLE 15

3-Dimethylamino-1-phenyl-1-m-trifluoromethyphenyl-propan-2-ol

An identical sequence of reactions to those described in Example 10 was used to convert m-trifluoromethyl-benzophenone to 3-dimethylamino-1-phenyl- 1-m-trifluoromethyl-phenyl-propan-2-ol isolated as the hydrochloride (5%), m.p. 110°– 113°,

EXAMPLE 16

3-Dimethylamino-1-p-methoxyphenyl-1-phenyl-propan-2-ol

An identical sequence of reactions to those described in Example 10 was used to convert p-methoxybenzophenone to 3-dimethylamino-1-p-methoxyphenyl-1-phenyl-propan-2-ol isolated as the hydrochloride (13%) as a glass.

EXAMPLE 17

3-Dimethylamino-1-o-chlorophenyl-1-phenyl-propan-2-ol

An identical sequence of reactions to those described in Example 10 was used to convert o-chlorobenzophenone to 3-dimethylamino-1-o-chlorophenyl-1-phenyl-propan-2-ol isolated as the hydrochloride (34%), m.p. 216° – 218° (from ethanol-ether).

EXAMPLE 18 b 3-Dimethylamino-1-m-bromophenyl-1-phenyl-propan-2-ol

An identical sequence of reactions to those described in Example 10 was used to convert m-bromobenzophenone to 3-dimethylamino-1-m-bromophenyl-1-phenyl-propan-2-ol isolated as the hydrochloride (22%), m.p. 128°– 138° (from ethanol-ether).

EXAMPLE 19

3-Dimethylamino-1-(3,4-dichlorophenyl)-1-phenyl-propan-2-ol

An identical sequence of reactions to those described in Example 10 was used to convert 3,4-dichlorobenzophenone to 3-dimethylamino-1-(3,4-dichlorophenyl)-1-phenyl-propan-2-ol isolated as the hydrochloride (3%) as a glass.

EXAMPLE 20

-(N-Methyl-N-ethylamino)-1,1--diphenyl-propan-2-ol-

Sodium borohydride (1 52g) in sodium hydroxide solution (15ml 0.02M) was added to 1,1-diphenyl-3-bromo-propan-2-one (12g) in methanol (50 ml) and the solution was stirred for one hour. Isolation through ether in the usual manner afforded 1,1-diphenyl-3-bromo-propan-2-ol (10 4g 86%) as an oil, Excess N methyl-N-ethylamine was added to a solution of 1,1-diphenyl-3-bromo-propan-2-ol (2g) in ethanol. After 60 hours the solution was evaporated and the residue dissolved in dilute hydrochloric acid and ether. Basificiation of the acid extract and subsequent isolation through ether in the usual manner gave 3-(N-methyl-N-ethylamino)-1,1-diphenyl-propan-2-ol isolated as the hydrochloride (1 25g, 60%), m.p. 159°– 161°.

EXAMPLE 21

-N-Piperidino-1,1-diphenyl-propan-2-ol

Diphenylacetaldehyde was converted to 1,1-diphenyl-2,3-epoxy-propan (90%) using dimethylsulphoxonium methylide by the procedure described in Example 8. Further reaction of the epoxide with piperidine, also as described in Example 8 gave 3-N-piperidino-1,1-diphenyl-propan-2-ol isolated as the hydrochloride (57%), m.p. 194° – 196°.

EXAMPLE 22

2-Benzoyloxy-3-dimethylamino-1,1-diphenyl-propane

Benzoyl chloride (1 49g) was added to 3-dimethylamino-1,1-diphenyl-propan-2-ol (2,55g) in dry pyridine (10 ml.) and the solution allowed to stand for 4 hours. Pyridine was removed by evaporation and the residue dissolved in dilute hydrochloric acid and ether. Basification of the acid extract and isolation through ether in the usual manner gave 2-benzoyloxy-3-dimethylamino-1,1-diphenyl-propane (3.47g . 99%), m.p. 90°– 91°.

EXAMPLE 23
3-Benzylamino-1,1-diphenyl-propan-2-ol 1,1-Diphenyl-2,3-epoxy-propane, prepared as described in EXAMPLE 21 was reacted with benzylamine in ethanol by a procedure analogous to that described in Example 8, 3-benzylamino-1,1-diphenyl-propan-2-ol (33%), m.p. 123°-124° was obtained.

EXAMPLE 24
-Dimethylamino-1,1-diphenyl-propan-2-ol (a) 2-Acetoxy-3-dimethylamino- 1,1-diphenyl-propane 8200mg) was dissolved in methanolic potassium hydroxide (5% 10 ml) and the solution allowed to stand overnight. Solvent was evaporated and the residue dissolved in ether and water. The ether extract was dried and evaporated to give 3-dimethylamino-1,1- diphenyl-propan-2-ol (170 mg, 97%), m.p. 72°- 73°

(b) 1,1-Diphenyl-3-bromopropan-2-ol (500mg) prepared as described in Example 20 was treated with excess dimethylamine in ethanol and the solution allowed to stand overnight. Solvent was removed by evaporation and the residue dissolved in dilute hydrochloric acid and ether. Basification of the acid extract and isolation through ether in the usual manner gave 3-dimethylamino-1,1-diphenyl-propan-2-ol (330mg, 75%) m p 72° - 73°.

(c) 1,1-Diphenyl-2,3-epoxy-propane prepared as described in Example 21, was further reacted with dimethylamine in ethanol by the procedure described in Example 8 to give 3-dimethylamino-1,1-diphenyl-propan-2-ol (90%) m p 72° - 73°.

EXAMPLE 25
4-Diethylaminobutyrate of 3-dimethylamino-1,1-diphenyl-propan-2-ol A solution of 3-dimethylamino-1,1-diphenyl-propan-2-ol (2 55g), 4-diethylaminobutyric acid hydrochloride (1 95g) and dicyclohexylcarbodiimide (2 1g) in dichloromethane (50 ml) was stirred at room temperature for 5 days. Dicyclohexylurea was filtered off and the filtrate concentrated. The residue was dissolved in dilute hydrochloric acid and ether. The acid extract was basified; isolation through ether in the normal manner gave an oil which was chromatographed as alumina (200g.). Elution with progressively graded mixtures of light petroleum and ether gave the 4-diethylaminobutyrate of 3-dimethylamino-1,1-diphenyl-propan-2-ol isolated as the dihydrochloride (41%) as a glass.

EXAMPLE 26
(−)-3-Dimethylamino-1,1-diphenyl-propan-2-ol

Equimolar quantities of 3-dimethylamino-1,1-diphenyl-propan-2-ol and D(−)-mandelic acid were dissolved in ethyl acetate and the solution evaporated. The resulting mandelate was recrystallized 5 times from ethyl acetate using 30-35 mls of ethyl acetate per gram of mandelate, the melting point rising from 140°-143° to a constant 153°-154°. Regeneration of the free base gave (−)-3-dimethylamino-1,1-diphenyl-propan-2-ol, m.p. 61°-62°, $[\alpha]_D^{20}$ −45° (c 1.6 in EtOH) converted to the hydrobromide, m p 184° - 185°.

EXAMPLE 27
(+)-(3-Dimethylamino-1,1-diphenyl-propan-2-ol

The mother liquors from the preparation of the (−) isomer in Example 25 were combined and evaporated. The free base enriched (+)isomer, was regenerated in the usual manner. Equimolar quantities of free base and D(+)-mandelic acid were dissolved in ethyl acetate and the solution evaporated. The resulting mandelate was recrystallized 4 times from ethyl acetate using 30-35 mls of ethyl acetate per gram of mandelate, the melting point rising to a constant 153°-154°. Regeneration of the free base gave (±)-3-dimethylamino-1,1-diphenyl-propan-2-ol, m.p. 60°-61°, $[\alpha]_D^{20}$ + 56° (c 1.6 in EtOH) converted to the hydrobromide, m p 184° - 185°.

EXAMPLE - PHARMACOLOGY 1 a. Tests Used

1 Prevention of Reserpine Hypothermia for Potential Antidepressant

The method of Spencer [Antidepressant Drugs, 194 (1967)] was used. Groups of ten mice are given oral doses of test compound 24 18 and 2 hours before an intravenous injection of reserpine base (Serpasil). Oral temperatures of the mice are taken immediately before administration of reserpine and then 2, 4, 6 and 24 hours afterwards.

Mean temperatures of groups given test compounds are compared with reserpinised controls using a Students t test. Compounds causing a significant difference at the level $P < 0.001$ are considered active. In order to quantify anti-reserpine activity cumulative temparature differences from controls at 6 hours and 24 hours ($\Delta^6$ and $\Delta^{24}$) are calculated. Thus, the larger the figure for $\Delta^6$ and $\Delta^{24}$ the more active the compound $\Delta^6$ should be at least 5° C for the compound to be considered active and at least 8° C to have a highly acceptable level of activity 2 Reversal of Reserpine Hypothermia Groups of ten mice are injected intravenously with 1.5 mg/kg Reserpine base. Seventeen hours later the oral temperature of the mice are taken and various doses of test compound or vehicle given subcutaneously. Temperatures are taken 1, 2, 4, 6 and 24 hours later and the results are analysed as in Test 1 (The subcutaneous route is used for convenience as the very depressed reserpinised mice cannot be reliably dosed orally).

3 Inhibition of Noradrenaline and 5-Hydroxytryptamine Uptake in vitro

Synaptosomes are isolated from the brains of male Wistar rats (150-170g.) and monoamine uptake determined by the method of Snyder and Coyle (1968) [Snyder S. H. and Coyle J. T. J. Pharmac exp Ther 165 (1968) 76-86]. Uptake was determined over a ten minute period instead of the normal five minutes.

4 Mydriatic Response in Mice

Groups of five mice are pre-selected for uniformity of pupil diameter using a binocular microscope with a calibrated eye-piece. Pupil sizes are measured at various intervals after an intraperitoneal injection of test compound and at the peak time a curve plotted of percentage increase in pupil diameter versus log dose. From this the dose causing a 200% increase in pupil size (this lies on the linear part of the curve) is found.

(Anticholinergic compounds cause an increase in pupil diameter (nydriasis) thus the higher the dose quoted, the lower the probable side effect).

$pA_2$ Determination on Guinea Pig Illeum

This experiment measures in vitro antagonism to Acetylcholine (a possible side effect) and the lower the $pA_2$ the more desirable the compound. $pA_x$ is defined as the negative logarithm base 10 of the molar concentration of antagonist which will reduce the effect of a multiple dose (X) of an active drug to that of a single dose. It is thus a means of expressing anticholinergic activity which is independent of the dose of Acetylcholine and the piece of tissue used.

The method used is similar to that of Schild, [Brit. J Pharmacol 14 (1959) 48], the tissue being bathed in Tyrode solution and a dose response curved for Acetylcholine being obtained. This dose response curve is repeated in the presence of various doses of test compound and the $pA_2$ is found rom a plot (log dose ratio-1) against molar concentration of the test compound.

Animals and Solutions

Carworth Europe male mice are used for all experiments apart from that using the cat nictitating membrane and test compounds are administered orally as solutions in distilled water. Compounds for intravenous administration are dissolved in 0 9% saline apart from Reserpine which is dissolved in dilute acetic acid buffered to pH5. Unless otherwise stated, the dosing interval is one hour.

b. Results

Prevention of Reserpine Hypothermia

Compounds of the formulae E1 and E2:

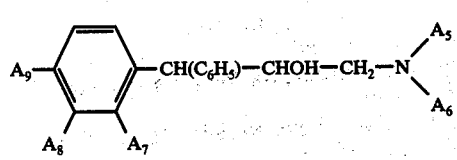
(E1)

$(Ph)_2(CH — CA_{10}OA_{11} — CH_2 — A_{12} — HCl$ (E2)

and the standard compounds Imiprimine and Amitryptyline were tested as described in a1. The results are shown in Tables 1 and 2.

TABLE I

| $A_5$ | $A_6$ | $A_7$ | $A_8$ | $A_9$ | Salt | Reserpine Prevention Test | | |
|---|---|---|---|---|---|---|---|---|
| | | | | | | Dose mg/kg | $\Delta^6$(° C) | $\Delta^{24}$(° C) |
| $CH_3$ | $CH_3$ | H | H | H | HBr | 20 | 13 | 19 |
| $CH_2C_6H_5$ | $CH_3$ | H | H | H | HCl | 30 | 10 | 11 |
| $CH_2C_6H_5$ | $CH_3$ | H | H | F | HCl | 30 | 9 | 11 |
| $CH_3$ | $CH_3$ | H | H | F | | 20 | 11 | 15 |
| H | $CH_3$ | H | H | F | | 30 | 12 | 21 |
| $CH_3$ | $CH_3$ | H | H | Cl | | 30 | 13 | 22 |
| $CH_3$ | $CH_3$ | H | Cl | H | HCl | 20 | 10 | 17 |
| $CH_3$ | $CH_3$ | $CH_3$ | H | H | HCl | 30 | 11 | 14 |
| $CH_3$ | H | H | H | $CH_3$ | HCl | 100 | 6 | 6 |
| $C_2H_5$ | $C_2H_5$ | H | H | H | HCl | 30 | 11 | 11 |
| $CH_3$ | H | H | H | H | HCl | 20 | >10 | >10 |

TABLE 2

| $A_{10}$ | $A_{11}$ | $A_{12}$ | Reserpine Prevention Test | | |
|---|---|---|---|---|---|
| | | | Dose mg/kg | $\Delta^6$(° C) | $\Delta^{24}$(° C) |
| $CH_3$ | H | $NHCH_3$ | 30 | 7 | 13 |
| $CH_3$ | H | $N(CH_3)CH_2C_6H_5$ | 100 | 6 | 8 |
| H | H | morpholino | 100 | 10 | 10 |
| H | H | piperidine | 100 | 9 | 10 |
| H | $COCH_3$ | $N(CH_3)_2$ | 20 | >10 | >10 |

TABLE 2-continued

| $A_{10}$ | $A_{11}$ | $A_{12}$ | Reserpine Prevention Test | | |
|---|---|---|---|---|---|
| | | | Dose mg/kg | $\Delta^6$(° C) | $\Delta^{24}$(° C) |
| Imiprimine hydrochloride | | | 30 | 10 | 17 |
| Amitriptyline hydrochloride | | | 30 | 12 | 22 |

2 Reversal of Reserpine Hypothermia

Using the test described in a2, the following results were found for certain compounds of formula E1 :

TABLE 3

| $A_5$ | $A_6$ | $A_7$ | $A_8$ | $A_9$ | Salt | Reserpine Reversal Test | | |
|---|---|---|---|---|---|---|---|---|
| | | | | | | Dose mg/kg | $\Delta^6$(° C) | $\Delta^{24}$(° C) |
| $CH_3$ | $CH_3$ | H | H | H | HBr | 20 | 14 | 22 |
| $CH_3$ | $CH_3$ | H | H | F | HCl | 25 | 17 | 23 |
| $CH_3$ | $CH_3$ | H | H | Cl | | 30 | 9 | 11 |
| Imipramine | | | | | HCl | 10 | 18 | 18 |

3 Inhibition of Noradrenaline and 5-Hydroxytryptamine

Using the test described in a3, the following results were found for certain compounds of formula E1 :

TABLE 4

| $A_5$ | $A_6$ | $A_7$ | $A_8$ | $A_9$ | Salt | Inhibition of Monoamine Uptake | | |
|---|---|---|---|---|---|---|---|---|
| | | | | | | Molar Concentration | NA (%) | 5HT (%) |
| H | $CH_3$ | H | H | H | HCl | $10^{-5}$ | 85 | |
| | | | | | | $10^{-6}$ | 65 | |
| $CH_3$ | $CH_3$ | H | H | F | | $10^{-5}$ | 80 | 85 |
| | | | | | | $10^{-6}$ | 59 | 60 |
| Imipramine | | | | | HCl | $10^{-5}$ | 85 | 90 |
| | | | | | | $10^{-6}$ | 56 | 55 |

4 Mydriatic Response in Mice and $pA_2$ in Guinea Pigs

Compounds of the formula E1 were tested as described in a4 and a5 to provide the results shown in Table 5

TABLE 5

| $A_5$ | $A_6$ | $A_7$ | $A_8$ | $A_9$ | Salt | Anticholinergic Side Effect | |
|---|---|---|---|---|---|---|---|
| | | | | | | Mydriasis-Dose to cause 200% effect-mg/kg | $pA_2$ on Illium |
| $CH_3$ | $CH_3$ | H | H | H | HBr | 41 | 5 |
| H | $CH_3$ | H | H | H | HCl | 114 | 5 |
| $CH_3$ | H | H | H | F | HCl | 92 | 4 |
| $CH_3$ | $CH_3$ | H | H | Cl | HCl | 40 | 5 |
| Imipramine | | | | | HCl | 18 | 9 |
| Amitryptyline | | | | | HCl | 6 | 8 |

EXAMPLE - PHARMACOLOGY 2 a. Test Used

The Reserpine Prevention, Reserpine Reversal and Noradrenaline Uptake Inhibition tests were carried out as described in the previous Example. The Mydriasis test was also as described in the previous Example but using 20 mg/kg doses of each compound after which a curve was plotted of percentage increase in pupil diameter versus time and the percentage increase was integrated with respect to time for 0-120 minutes after dosing and the result expressed as a percentage.

b. Results ($\pm$)-3-Dimethylamino-1,1-diphenylpropan-2-ol is Compound A (+)-3-Dimethylamino-1,1-diphenylpropan-2-ol is Compound B (−)-3-Dimethylamino-1,1-diphenylpropan-2-ol is Compound C

| Compound | Inhibition of Noradrenaline Uptake In Vitro | | Mydriasis Integral Percent 120 Mins. | |
|---|---|---|---|---|
| | Molar Conc. | % | Dose | % |
| A | $10^{-6}$ | 63 | 20mg/kg. | 7400 |
| B | $10^{-6}$ | 40 | 20mg/kg. | 12600 |
| C | $10^{-6}$ | 64 | 20mg/kg. | 6700 |

| Compound | Dose | Reserpine Prevention | | Reserpine Reversal | |
|---|---|---|---|---|---|
| | | $\Delta^6(°C)$ | $\Delta^{24}(°C)$ | $\Delta^6(°C)$ | $\Delta^{24}(°C)$ |
| A | 10 | 12 | 16 | 16 | 20 |
| | 20 | 15 | 19 | 14 | 17 |
| | 40 | 15 | 22 | 15 | 20 |
| B | 10 | 12 | 15 | 16 | 27 |
| | 20 | 16 | 23 | 15 | 19 |
| | 40 | 16 | 25 | 13 | 19 |
| C | 10 | 11 | 17 | 6 | 3 |
| | 20 | 13 | 19 | 16 | 19 |
| | 40 | 12 | 19 | 13 | 20 |

These results indicate that the (−)-isomer shows fewer peripheral anticholinergic effects than the (+)-isomer and that (+)-isomer is more active than the (−)-isomer on the Reserpine Reversal Test at low doses but that the two isomers have roughly equal effects on the Reserpine Prevention tests.

What we claim is:

1. A compound of the formula

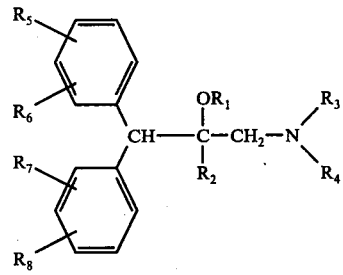

or a pharmaceutically acceptable salt or hydrate thereof or mixtures of optical isomers of the above formula, wherein $R_1$ is $CO.R_9$ wherein $R_9$ is alkyl of 1 to 6 carbon atoms, phenyl or benzyl; $R_2$ is hydrogen; $R_3$ is hydrogen or methyl; $R_4$ is methyl; $R_5$ is fluorine, chlorine or bromine; and $R_6$, $R_7$ and $R_8$ are each hydrogen.

2. A compound according to claim 1 wherein $R_9$ is alkyl of 1 to 6 carbon atoms.

3. A compound according to claim 1 wherein $R_9$ is methyl or ethyl.

4. A compound according to claim 1 wherein $R_9$ is methyl.

5. A compound according to claim 1 wherein $R_5$ is 4-fluorine and $R_9$ is methyl.

6. A compound according to claim 1 wherein $R_5$ is 3-chlorine and $R_9$ is methyl.

7. A compound according to claim 1 wherein $R_5$ is 4-chlorine and $R_9$ is methyl.

8. A compound according to claim 1 wherein $R_5$ is 3-bromine and $R_9$ is methyl.

9. A compound according to claim 1 in the form of a single optical isomer.

10. A compound according to claim 1 in the form of a mixture of optical isomers.

11. A compound of the formula (III):

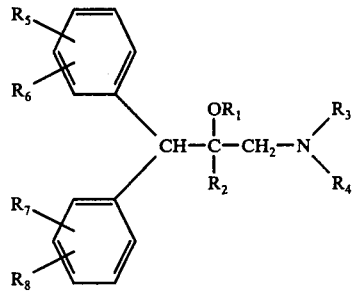

or a pharmaceutically acceptable acid addition salt thereof or mixtures of optical isomers of the above formula wherein $R_1$ is $CO.R_9$ wherein $R_9$ is alkyl of 1-6 carbon atoms, phenyl or or benzyl; $R_2$ is hydrogen; $R_3$ is hydrogen or methyl; $R_4$ is methyl; $R_5$ is trifluoromethyl; and $R_6$, $R_7$ and $R_8$ are each hydrogen.

12. A compound according to claim 11 wherein $R_9$ is alkyl of 1 to 6 carbon atoms.

13. A compound according to claim 11 wherein $R_9$ is methyl or ethyl.

14. A compound according to claim 13 wherein $R_9$ is methyl.

15. A compound according to claim 11 wherein $R_5$ is 3-trifluoromethyl and $R_9$ is methyl.

* * * * *